United States Patent [19]

Niwata et al.

[11] Patent Number: 5,039,696
[45] Date of Patent: Aug. 13, 1991

[54] MALEIMIDE DERIVATIVES AND FUNGICIDES FOR AGRICULTURE AND HORTICULTURE CONTAINING THE SAME

[75] Inventors: Shinjiro Niwata, Toyonaka; Harukazu Fukami, Kyoto; Masaki Hashimoto, Ibaraki; Norio Ohtsuka, Hitatsuka; Fumio Fujita, Yokohama, all of Japan

[73] Assignee: Suntory Limited, Osaka, Japan

[21] Appl. No.: 473,632

[22] Filed: Feb. 1, 1990

[30] Foreign Application Priority Data

Feb. 6, 1989 [JP] Japan .................................. 1-25863

[51] Int. Cl.$^5$ .................. A01N 43/36; C07D 207/456
[52] U.S. Cl. ................................. 514/425; 548/547; 548/548
[58] Field of Search ................. 548/548, 547; 514/425

[56] References Cited

FOREIGN PATENT DOCUMENTS 0117482 9/1984 European Pat. Off. .
0319712 6/1989 European Pat. Off. .
2300913 7/1973 Fed. Rep. of Germany .
1145583 3/1969 United Kingdom .

OTHER PUBLICATIONS

J. Am. Chem. Soc., 67, 308 (1945), Organic Synthesis Handbook (Japanese), pp. 1100-1101.
J. Prakt. Chemie, 327 (5), p. 857.
The Journal of Organic Chemistry, vol. 327, No. 5, pp. 857-864.
Chemical Abstracts, vol. 99, No. 21, Abst. No. 172332V.

Primary Examiner—David B. Springer
Attorney, Agent, or Firm—Burns, Doane, Swecker & Mathis

[57] ABSTRACT

A maleimide derivative useful as an active agent for a fungicide for agriculture and horticulture, having the formula (I):

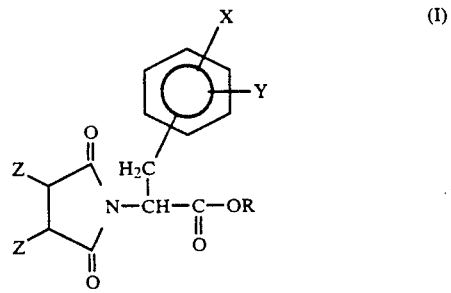

wherein
X and Y each independently represent a hydrogen atom, a halogen atom, a hydroxyl group, a lower alkyl group, a lower alkoxy group, an aralkyloxy group or a trifluoromethyl group,
Z represents a chlorine atom or bromine atom,
and R represents a straight or branched alkyl group having 1 to 15 carbon atoms, an alkenyl group having 2 to 5 carbon atoms, an alkynyl group having 2 to 5 carbon atoms, an alkoxyalkyl group having 2 to 5 carbon atoms, an oxoalkyl group having 3 to 6 carbon atoms or a phenyl group or a phenyl alkyl group which may be substituted.

14 Claims, No Drawings

MALEIMIDE DERIVATIVES AND FUNGICIDES FOR AGRICULTURE AND HORTICULTURE CONTAINING THE SAME

BACKGROUND OF THE INVENTION

1. Field of the Invention

The present invention relates to a novel maleimide derivative having the formula (I):

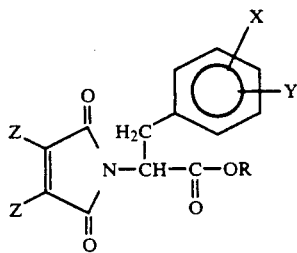

wherein

X and Y each independently represent a hydrogen atom, a halogen atom, a hydroxyl group, a lower alkyl group having 1 to 3 carbon atoms, a lower alkoxy group having 1 to 3 carbon atoms, an aralkyloxy group having 7 to 10 carbon atoms, or a trifluoromethyl group, Z represents a chlorine atom or bromine atom, and R represents a straight or branched alkyl group having 1 to 15 carbon atoms, an alkenyl group having 2 to 5 carbon atoms, an alkynyl group having 2 to 5 carbon atoms, an alkoxyalkyl group having 2 to 5 carbon atoms, an oxoalkyl group having 3 to 6 carbon atoms or a phenyl group which may be substituted with a halogen atom, $C_1-C_3$ alkyl group or $C_1-C_3$ haloalkyl group or a phenyl $C_1-C_3$ alkyl group which may be substituted with a halogen atom, $C_1-C_3$ alkyl group or $C_1-C_3$ haloalkyl group, and a fungicide for agriculture and horticulture containing the same as the active ingredient.

2. Description of the Related Art

Concerning maleimide derivatives having amino acid as the skeleton, for example, J. Prakt. Chemi., 327 (5), p. 857–864 describes the compound shown below:

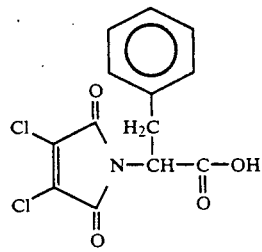

This article however, does not disclose whether or not this compound has a fungicidal activity.

SUMMARY OF THE INVENTION

The object of the present invention is to develop novel compounds having a new skeleton with preventive and therapeutical controlling effects on various plant diseases.

Other objects and advantages of the present invention will be apparent from the following description.

In accordance with the present invention, there is provided a novel maleimide derivative having the above-mentioned formula (I).

In accordance with the present invention, there is also provided a fungicide composition for agriculture and horticulture comprising the above-mentioned maleimide derivative as an active ingredient and a carrier therefor.

DESCRIPTION OF THE PREFERRED EMBODIMENTS

In the above-mentioned formula (I), representative examples of the halogen atom of the substituents X and Y may include 4-chloro, 2-dichloro, 3,5-dichloro, 2-fluoro, 3-fluoro, 4-fluoro, 2,4-difluoro, 2,6-difluoro, 2-chloro-4-fluoro and 3,5-difluoro groups, representative examples of the lower alkyl group may include a 2,6-dimethyl group, representative examples of the lower alkoxy groups may include 4-methoxy, ethoxy and propyloxy groups, and representative examples of the aralkyloxy group may include benzyloxy phenyloxy and naphthyloxy groups. Representative examples of the straight or branched alkyl group having 1 to 15 carbon atoms may include methyl, ethyl, n-propyl, isopropyl, n-butyl, sec-butyl, isobutyl, t-butyl, 3,3-dimethyl-butyl, n-heptyl, and myristyl groups, representative examples of the alkenyl group having 2 to carbon atoms may include vinyl 1-propenyl, allyl, insopropenyl, 2-butenyl, and 2-pentenyl groups, representative examples of the alkynyl group having 2 to carbon atoms may include ethynyl, propargyl, butynyl, and penthynyl groups, representative examples of the alkoxyalkyl group may include methoxyethyl and ethoxyethyl groups, representative examples of the oxoalkyl group having 3 to 6 carbon atoms may include acetonyl, 3-oxobutyl, and 2-oxo-3,3-dimethylbutyl groups, and representative examples of the phenyl group or phenylalkyl group, which may be substituted, may include 2,6-dimethylphenyl, 3,5-dichlorophenyl, 2-trifluoromethylphenyl, benzyl, 2,6-dimethylbenzyl, 3,5-dichlorobenzyl, and 2-trifluoromethylbenzyl 2,6-dimethylphenetyl and 3,5-dichlorophenylpropyl groups.

The maleimide derivative having the above-mentioned formula (I) according to the present invention can be prepared by the following reaction route, using, for example, an amino acid as the starting material.

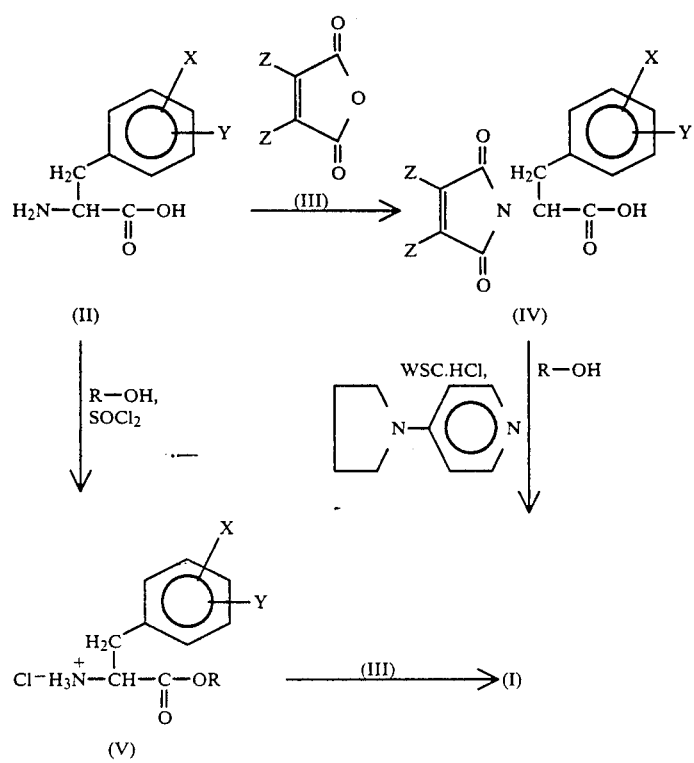

In the above-mentioned formulae, X, Y, Z and R are the same as defined in the formula (I).

Thus, the amino acid represented by the formula (II) can be reacted with a maleic anhydride derivative (III) in an organic solvent such as acetic acid, at a temperature of room temperature to around the boiling point of the solvent, to give a compound represented by the formula (IV) as the product. The carboxylic acid (IV) thus obtained can be esterified in conventional manner by using an alcohol (R-OH) to prepare the desired compound (I). Also, by suspending the amino acid (II) in the alcohol (R-OH) at a temperature of 0° C. to 60° C., while stirring, and carrying out the reaction by adding thionyl chloride dropwise to the suspension, an aminoester hydrochloride represented by the formula (V) can be obtained. The desired compound (I) also can be prepared by first subjecting this product to the action of triethylamine in an ether type organic solvent such as tetrahydrofuran, and then carrying out the reaction with the maleic anhydride derivative (III) in an organic solvent such as acetic acid at a temperature of room temperature to around the boiling point of the solvent.

The compound having the formula (I) obtained by the method as described above exhibits preventive and therapeutical effects against diseases of plants as a fungicide for agriculture and horticulture utilized by soil application or by stalk and leaf spraying, and is particularly effective against rice blast, wheat leaf rust, and late blight tomato, etc.

The compound of the present invention can be used as a mixture with a carrier or other auxiliary agents, if necessary, in the preparation forms conventionally used for a fungicide for agriculture and horticulture, such as a powder, coarse powder, fine powder, granules, wettable agent, emulsion, suspension, and aqueous solution. Suitable liquid carriers include, for example, water, alcohols such as ethanol and ethylene glycol, ketones such as acetone, ethers such as dioxane and cellosolve, aliphatic hydrocarbons such as kerosene and coal oil, aromatic hydrocarbons such as benzene and toluene, halogenated hydrocarbons such as chloroform and carbon tetrachloride, esters such as ethyl acetate and fatty acid glycerides, nitriles such as acetonitrile, and dimethylformamide and dimethyl sulfoxide.

Examples of suitable solid carriers to be used for the fungicide for agriculture and horticulture of the present invention include vegetable powder (e.g. starch, wheat powder, etc.), and mineral powder (e.g. kaoline, bentonite, calcium phosphate, clay, talcs, silicas, etc.), and these can be used alone or as a mixture of two or more thereof.

Also, as the emulsifier, spreader, penetration agent, and dispersing agent, surfactants such as soaps, sulfuric acid esters of higher alcohols, alkylsulfonic acids, alkylarylsulfonic acids, quaternary ammonium salts, oxylalkylamines, fatty acid esters, polyalkyleneoxide type, and anhydrosorbitol type can be widely used, and preferably are contained in an amount generally of about 0.2 to 10% (% denotes % by weight, as hereinafter the same). Other kinds of fungicide, insecticides, nematocides, herbicides, plant growth controllers, plant nutrients, fertilizers, and solid improvers can be mixed therewith, if desired.

The fungicide for agriculture and horticulture of the present invention can be prepared by known methods or methods similar thereto from the maleimide derivative (I), the carrier, and the auxiliary components as described above. The ratio (% by weight) of the compound in the control drug in the present invention is preferably about 5 to 90% in an emulsion and wettable agent, about 0.1 to 20% in an oil agent and powder, and about 1 to 50% in granules. Emulsions and wettable agents, etc., are preferably further diluted to a strength (e.g., 50 to 5000-fold) appropriate for spraying.

The amount of the compound (I) of the present invention, or the combinations in which other kinds of drugs are mixed, and the formulation ratio thereof may differ depending on various conditions such as the growth stage, growth location of the plant to be treated, kind of the disease microorganism, state of onset of a disease, and application time or application method of the drugs, but can be adjusted so that the about 10 to 300 g of the compound (I) covers 10 ares. The concentration of the compound (I) used can be within the range of from 10 to 1000 ppm, and the use method can be spraying, powder spraying, flooding or powder coating of seeds. The present invention is not limited by the application of a kind of use amount, use concentration or use method, provided that the compound can be safely and effectively applied to crops.

EXAMPLE

The present invention will now be further illustrated in detail by, but is by no means limited to, the following Examples, wherein "parts" are all by weight unless otherwise noted.

Example 1

Preparation of n-propyl (S)-3,4-dichloro-2,5-dihydro-2,5-dioxo-α-(phenylmethyl)-1H-pyrrole-1-acetate (Compound No. 3)

A suspension of 2.0 g of L-phenylalanine in 30 ml of n-propyl alcohol was heated to 50° C., 3.5 ml of thionyl chloride added thereto, and the reaction then continued for 5 hours until the L-phenylalanine crystals were dissolved. After completion of the reaction, the mixture was concentrated under a reduced pressure to obtain crude crystals. These crystals were then recrystallized from a solvent mixture of methanol-ether to give 2.93 g of L-phenyl alanine n-propyl ester hydrochloride as colorless crystals (yield: 99%).

The hydrochloride thus obtained (1.0 g) was dissolved in 25 ml of tetrahydrofuran and allowed to react with 1.2 ml of triethylamine at room temperature for 30 minutes, the precipitated crystals were separated by filtration, and the filtrate concentrated under a reduced pressure to give a colorless oily product. This oily product and 700 mg of dichloromaleic anhydride were dissolved in 6 ml of acetic acid and refluxed for 3 hours, and after completion of the reaction, the reaction mixture was concentrated under a reduced pressure, the residue was dissolved in ethyl acetate, washed with water, and dried over magnesium sulfate, followed by evaporation of the solvent. The residue obtained was purified by silica gel chromatography (eluant: n-hexane-ethyl acetate=9/1) to give 1.41 g of the desired compound as a colorless oily product (yield: 97%).

Example 2

Preparation of isopropyl (S)-3,4-dichloro-2,5-dihydro-2,5-dioxo-α-(phenylmethyl)-1H-pyrrole-1-acetate (Compound No. 4)

A solution of 2.0 g of l-phenylalanine and 2.2 g of dichloromaleic anhydride in 20 ml of acetic acid was refluxed for 3 hours, and after completion of the reaction, the reaction mixture was concentrated under a reduced pressure, and the crystals obtained were washed with a solvent mixture of ether and n-hexane to give 3.80 g of (S)-3,4-dichloro-2,5-dihydro-2,5-dioxo-α-(phenylmethyl)-1H-pyrrole-acetic acid as pale orange crystals (yield: 100%).

Then, 300 mg of isopropyl alcohol was added to a solution of 1.0 g of the carboxylic acid thus obtained, 700 mg of 1-(3-dimethylaminopropyl)-3-ethylcarbodiimide hydrochloride (WSC.HCl) and 40 mg of 4-pyrrolidinopyridine in 30 ml of dichloromethane, and the reaction was carried out under room temperature for 3 hours. After completion of the reaction, the reaction mixture was washed with water and dried over magnesium sulfate, followed by evaporation of the solvent under a reduced pressure. The residue obtained was purified by silica gel chromatography (eluant: n-hexane-ethyl acetate=9/1) to give 1.0 g of the desired compound as a pale yellow oily product (yield: 88%).

The compound Nos. and the physical property values of the compounds synthesized according to the method of Example 1 or Example 2 are shown in Table 1. The abbreviations in Table 1 are as shown below.

Me: methyl group, Et: ethyl group, Pr: propyl group, Bu: butyl group, Ph: phenyl group, m.p.: melting point, $n_D^{25}$: refractive index

TABLE 1

Maleimide Derivative (I)

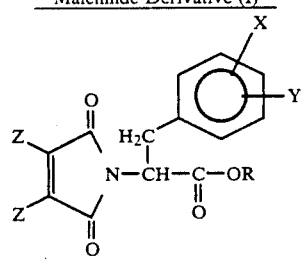

| Compound No. | —C$_6$H$_3$XY | R | Z | Configuration of α-position | Physical properties |
|---|---|---|---|---|---|
| 1 | Ph | Me | Cl | (S) | m.p. 42.0–43.0° C. |
| 2 | Ph | Et | Cl | (S) | $n_D^{25}$ 1.46828 |
| 3 | Ph | n-Pr | Cl | (S) | $n_D^{25}$ 1.46510 |
| 4 | Ph | i-Pr | Cl | (S) | $n_D^{25}$ 1.45696 |
| 5 | Ph | n-Bu | Cl | (S) | $n_D^{25}$ 1.41808 |
| 6 | Ph | i-Bu | Cl | (S) | $n_D^{25}$ 1.47992 |
| 7 | Ph | sec-Bu | Cl | (S) | $n_D^{25}$ 1.47580 |
| 8 | Ph | t-Bu | Cl | (S) | $n_D^{25}$ 1.43580 |
| 9 | Ph | —(CH$_2$)$_6$CH$_3$ | Cl | (S) | $n_D^{25}$ 1.48118 |

TABLE 1-continued

Maleimide Derivative (I)

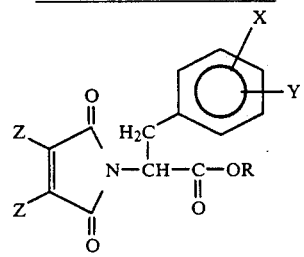

| | —C$_6$H$_3$XY | R | Z | Configuration of α-position | Physical properties |
|---|---|---|---|---|---|
| 10 | Ph | —(CH$_2$)$_{13}$CH$_3$ | Cl | (S) | m.p. 53.5–55.0° C. |
| 11 | Ph | 3,5-Cl$_2$Ph | Cl | (S) | Glassy |
| 12 | Ph | 2-CF$_3$Ph | Cl | (S) | m.p. 67.5–69.0° C. |
| 13 | Ph | 2,6-Me$_2$Ph | Cl | (S) | n$_D^{25}$ 1.46750 |
| 14 | Ph | —CH$_2$-4-ClPh | Cl | (S) | n$_D^{25}$ 1.48978 |
| 15 | Ph | —CH$_2$-3,5-Cl$_2$Ph | Cl | (S) | m.p. 120.4–120.8° C. |
| 16 | Ph | —CH$_2$-2-CF$_3$Ph | Cl | (S) | n$_D^{25}$ 1.47722 |
| 17 | Ph | —CH$_2$-2,6-Me$_2$Ph | Cl | (S) | m.p. 145.8–146.5° C. |
| 18 | Ph | —CH$_2$COCH$_2$Cl | Cl | (S) | m.p. 73.5–75.5° C. |
| 19 | Ph | —CH$_2$COCMe$_3$ | Cl | (S) | m.p. 85.8–86.8° C. |
| 20 | Ph | Et | Cl | (R) | n$_D^{25}$ 1.47198 |
| 21 | Ph | Et | Br | (S) | n$_D^{25}$ 1.47542 |
| 22 | Ph | —(CH$_2$)$_{13}$CH$_3$ | Br | (S) | m.p. 35.0–35.8° C. |
| 23 | 4-HOPh | Et | Cl | (S) | m.p. 123.5–124.0° C. |
| 24 | 4-MeOPh | Et | Cl | (S) | n$_D^{25}$ 1.47950 |
| 25 | 4-(PhCH$_2$O)Ph | Et | Cl | (S) | m.p. 64.5–64.8° C. |
| 26 | 2,6-Me$_2$Ph | Et | Cl | Racemic mixture | m.p. 95.5–96.5° C. |
| 27 | 4-ClPh | Et | Cl | " | n$_D^{25}$ 1.46858 |
| 28 | 4-ClPh | i-Bu | Cl | " | n$_D^{25}$ 1.46634 |
| 29 | 4-ClPh | —(CH$_2$)$_6$CH$_3$ | Cl | Racemic mixture | n$_D^{25}$ 1.45048 |
| 30 | 4-ClPh | 2,6-Me$_2$Ph | Cl | " | m.p. 166.0–168.0° C. |
| 31 | 4-ClPh | —CH$_2$-2-CF$_3$Ph | Cl | " | n$_D^{25}$ 1.46020 |
| 32 | 4-ClPh | —(CH$_2$)$_2$CMe$_3$ | Cl | " | n$_D^{25}$ 1.47754 |
| 33 | 4-ClPh | —(CH$_2$)$_2$OMe | Cl | " | n$_D^{25}$ 1.48610 |
| 34 | 4-ClPh | —CH$_2$C≡CH | Cl | " | m.p. 115.2–115.8° C. |
| 35 | 4-ClPh | —CH$_2$CH=CHCH$_3$ | Cl | " | n$_D^{25}$ 1.49502 |
| 36 | 4-ClPh | Et | Br | " | Glassy |
| 37 | 4-ClPh | n-Bu | Br | " | " |
| 38 | 2,4-Cl$_2$Ph | Et | Cl | " | n$_D^{25}$ 1.47320 |
| 39 | 2,4-Cl$_2$Ph | n-Bu | Cl | " | n$_D^{25}$ 1.47842 |
| 40 | 2,4-Cl$_2$Ph | Et | Br | " | n$_D^{25}$ 1.47718 |
| 41 | 2,4-Cl$_2$Ph | n-Bu | Br | " | n$_D^{25}$ 1.46288 |
| 42 | 3,5-Cl$_2$Ph | Et | Cl | " | n$_D^{25}$ 1.45056 |
| 43 | 3,5-Cl$_2$Ph | n-Bu | Cl | " | n$_D^{25}$ 1.46426 |
| 44 | 3,5-Cl$_2$Ph | Et | Br | " | m.p. 98.0–99.0° C. |
| 45 | 3,5-Cl$_2$Ph | n-Bu | Br | " | m.p. 86.6–87.5° C. |
| 46 | 2-FPh | Et | Cl | (S) | n$_D^{25}$ 1.47020 |
| 47 | 2-FPh | n-Bu | Cl | (S) | n$_D^{25}$ 1.48900 |
| 48 | 3-FPh | Et | Cl | (S) | m.p. 37.0–39.0° C. |
| 49 | 3-FPh | n-Bu | Cl | (S) | n$_D^{25}$ 1.49254 |
| 50 | 4-FPh | Et | Cl | (S) | m.p. 57.5–59.0° C. |
| 51 | 4-FPh | n-Bu | Cl | (S) | n$_D^{25}$ 1.47062 |
| 52 | 2-Cl-4-FPh | Et | Cl | Racemic mixture | Glassy |
| 53 | 2-Cl-4-FPh | n-Bu | Cl | " | n$_D^{25}$ 1.46104 |
| 54 | 2,6-F$_2$Ph | Et | Cl | " | Glassy |
| 55 | 2,6-F$_2$Ph | n-Bu | Cl | " | " |
| 56 | 2,4-F$_2$Ph | Et | Cl | " | n$_D^{25}$ 1.45562 |
| 57 | 2,4-F$_2$Ph | n-Bu | Cl | " | n$_D^{25}$ 1.48174 |
| 58 | 3,5-F$_2$Ph | Et | Cl | " | m.p. 86.0–87.0° C. |
| 59 | 3,5-F$_2$Ph | n-Bu | Cl | " | n$_D^{25}$ 1.48480 |
| 60 | 2-CF$_3$Ph | Et | Cl | (S) | n$_D^{25}$ 1.45876 |
| 61 | 2-CF$_3$Ph | n-Bu | Cl | (S) | n$_D^{25}$ 1.47494 |
| 62 | 2-CF$_3$Ph | i-Pr | Cl | (S) | n$_D^{25}$ 1.47040 |
| 63 | 4-CF$_3$Ph | Et | Cl | Racemic mixture | n$_D^{25}$ 1.44848 |
| 64 | 4-CF$_3$Ph | n-Bu | Cl | " | n$_D^{25}$ 1.46560 |
| Comparative Example | Ph | H | Cl | (S) | — |

Preparation Example 1 (Wettable agent)

A 10 parts amount of the compound (No. 2), 5 parts of sodium laurylsulfate, 2 parts of sodium dinaphthylmethanedisulfonateformalin condensate, and 83 parts of clay were mixed and crushed to obtain 100 parts of a wettable agent.

Preparation Example 2 (Powder)

A 0.2 parts amount of the compound (No. 2), 0.5 part of calcium stearate, 50 parts of talc, and 49.3 parts of clay were mixed and crushed to obtain 100 parts of powder.

Preparation Example 3 (Emulsion)

A 9 parts amount of the compound (No. 2), 10 parts of ethylene glycol, 20 parts of dimethylformamide, 10 parts of an alkyldimethylammonium chloride, and 52 parts of methanol were mixed and dissolved to obtain 100 parts of an emulsion.

Preparation Example 4 (Granule)

A 10 parts amount of the compound (No. 2), 15 parts of starch, 72 parts of bentonite, and 3 parts of sodium salt of a lauryl alcohol sulfuric acid ester were mixed and crushed to obtain 100 parts of granules.

Test Example 1 (Rice blast control effect test)

[Test method]

Thirty grains of unhulled rice (species: *Nipponbare*) after germination were directly seeded in a pot and grown to the second to third leaf stage in a greenhouse. The wettable agent prepared according to the method of Preparation Example 1 and diluted with water to a predetermined concentration was sprayed over the rice seedlings by a spray gun, in an amount of 30 ml per 3 pots, left to stand at room temperature for one day, and thereafter, a blast disease microorganism (*Pyricularia oryzae*) was inoculated thereto. The inoculation source was made into a suspension of the spores of the blast disease microorganism formed and grown on rice straw extract agar (spore concentration $5 \times 10^5$/ml), by spraying by a spray gun.

After inoculation, the seedlings were left to stand in a greenhouse at 26° C. for 24 hours, and then grown in a greenhouse at 25° C. for 7 days, while avoiding direct sunlight, to effect an onset of the disease. After the onset of the disease, the disease speckle number per pot was measured and the control value was calculated from the following formula:

$$\text{Control value} = \left(1 - \frac{\text{Total disease speckle number of treated area}}{\text{Total disease speckle number of non-treated area}}\right) \times 100$$

[Test results]

The control effects of the drugs provided for the tests are shown in Table 2.

TABLE 2

| Rice blast control effect test | | |
|---|---|---|
| Compound No. | Spray conc. (ppm) | Control value |
| 5 | 500 | 100.0 |
| 6 | 500 | 100.0 |
| 7 | 500 | 95.7 |
| 12 | 500 | 80.4 |
| 16 | 500 | 91.5 |
| 21 | 500 | 100.0 |
| 24 | 500 | 83.3 |
| 26 | 500 | 96.3 |
| 27 | 500 | 95.4 |
| 28 | 500 | 98.6 |
| 36 | 500 | 78.9 |
| 38 | 500 | 93.3 |
| 40 | 500 | 90.0 |
| 42 | 500 | 86.7 |
| 49 | 500 | 100.0 |
| 50 | 500 | 100.0 |
| 60 | 500 | 100.0 |

TABLE 2-continued

| Rice blast control effect test | | |
|---|---|---|
| Compound No. | Spray conc. (ppm) | Control value |
| 61 | 500 | 100.0 |
| 63 | 500 | 93.3 |
| 64 | 500 | 90.0 |
| Comparative Example | 500 | 0.0 |

Test Example 2 (Tomato late blight control effect test)

[Test Method]

The wettable agent prepared according to the method of Preparation example 1 was diluted with water to a predetermined concentration and sprayed in an amount of 30 ml per pot over tomato seedlings (species: Red cherry) (3 rows in one district) grown to the 5-th to 6-th stage after seeding, and one day after the drug treatment, the blight microorganism (*Phytophtora infestans*) was inoculated thereto. Zoospore cysts formed on the tomato leaves was scraped off, prepared to $1 \times 10^5$/ml as a zoospore cyst, maintained at 13° C. for about 1 hour, and after confirmation of an indirect germination of the zoospore (40% or more), spray inoculated by a spray gun. After inoculation, the zoospore was stored in a humid chamber at 20° C. for one day, and then maintained in a greenhouse at 25° C. for 2 days. The disease speckle area ratio for 3 to 4 leaves per one root was examined in 10 stages, and the control value was calculated.

$$\text{Control value} = \left(1 - \frac{\text{Disease onset index of treated area}}{\text{Disease onset index of non-treated area}}\right) \times 100$$

[Test results]

The control effects of the drugs provided for the test are shown in Table 3.

TABLE 3

| Tomato late blight control effect test | | |
|---|---|---|
| Compound No. | Spray concentration (ppm) | Control value |
| 3 | 500 | 80.9 |
| 7 | 500 | 90.0 |
| 18 | 500 | 100.0 |
| 21 | 500 | 85.4 |
| 23 | 500 | 88.9 |
| 24 | 500 | 91.1 |
| 27 | 500 | 100.0 |
| 42 | 500 | 82.2 |
| 46 | 500 | 97.8 |
| 47 | 500 | 84.4 |
| 48 | 500 | 98.9 |
| 49 | 500 | 88.9 |
| 50 | 500 | 97.8 |
| 51 | 500 | 92.2 |
| 60 | 500 | 88.9 |
| Comparative Example | 500 | 0.0 |

Test Example 3 (Wheat leaf rust control effect test)

[Test Method]

The wettable agent prepared according to the method of Preparation example 1 was diluted with water to a predetermined concentration and sprayed over wheat (species: Norin No. 61) (3 rows per one district) grown to 1st-leave stage after seeding, by an automatic spraying device in an amount of 30 ml per 3 pots, and a rust microorganism (*Puccinia recondita*) was inoculated thereto. For the inoculation source, summer spores obtained by mincing the afflicted leaves, pouring water onto the leaves, performing a sonication treatment twice, and filtering through a 4-ply gauze were used, and a spore suspension to $1 \times 10^5$/ml was prepared and inoculated. After inoculation, the leaves were maintained in a humid chamber at 24° C. for 24 hours, and then maintained in the white cold leno cloth in a glass greenhouse for 9 days. From the speckle number of 10 first leaves per one pot, the following disease index was given, the disease onset degree was determined according to the following formula, and the control value was calculated therefrom.

0: no onset of disease
1: disease speckle number 1 to 5
2: disease speckle number 6 to 10
3: disease speckle number 11 to 20
4: disease speckle number 21 or more Disease onset degree =

$$\frac{4 \times \text{(number of leaves of index 4)} + \ldots + 1 \times \text{(number of leaves of index 1)}}{4 \times 10} \times 100$$

Control value = 100 − (Disease onset degree)

[Test results]

The control effects of the drugs provided for the test are shown in Table 4.

TABLE 4

| | Wheat leaf rust control effect test | |
|---|---|---|
| Compound No. | Spray concentration (ppm) | Control value |
| 26 | 500 | 98.1 |
| 27 | 500 | 100.0 |
| 33 | 500 | 92.6 |
| 34 | 500 | 92.6 |
| 35 | 500 | 89.8 |
| 36 | 500 | 100.0 |
| 37 | 500 | 91.5 |
| 38 | 500 | 100.0 |
| 39 | 500 | 100.0 |
| 40 | 500 | 98.3 |
| 42 | 500 | 98.3 |
| 46 | 500 | 100.0 |
| 47 | 500 | 100.0 |
| 48 | 500 | 100.0 |
| 49 | 500 | 100.0 |
| 50 | 500 | 100.0 |
| 51 | 500 | 100.0 |
| 60 | 500 | 100.0 |
| 61 | 500 | 98.1 |
| 63 | 500 | 92.3 |
| Comparative Example | 500 | 67.5 |

We claim:

1. A maleimide derivative having the formula (I):

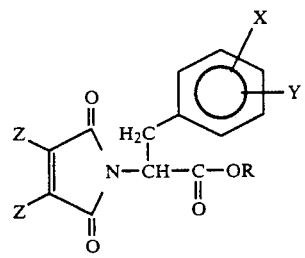

wherein
X and Y each independently represent a hydrogen atom, a halogen atom, a hydroxyl group, a lower alkyl group having 1 to 3 carbon atoms, a lower alkoxy group having 1 to 3 carbon atoms, an aralkyloxy group having 7 to 10 carbon atoms, or a trifluoromethyl group,
Z represents a chlorine atom or bromine atom,
and R represents a straight or branched alkyl group having 1 to 15 carbon atoms, an alkenyl group having 2 to 5 carbon atoms, an alkynyl group having 2 to 5 carbon atoms, an alkoxyalkyl group having 2 to 5 carbon atoms, an oxoalkyl group having 3 to 6 carbon atoms or a phenyl group which may be substituted with halogen atom, $C_1$–$C_3$ alkyl group or $C_1$–$C_3$ haloalkyl group or a phenyl $C_1$–$C_3$ alkyl group which may be substituted with halogen atom, $C_1$–$C_3$ alkyl group or $C_1$–$C_3$ haloalkyl group.

2. A fungicide composition for agriculture and horticulture, comprising a compound according to claim 1 as the active ingredient, and a carrier therefor.

3. The maleimide derivative of claim 1, wherein X represents a hydrogen atom, a chlorine atom, a fluorine atom or a trifluoromethyl group; Y represents a hydrogen atom or a chlorine atom; Z represents a chlorine atom or bromine atom; and R represents a lower alkyl group having 1 to 4 carbon atoms.

4. The maleimide derivative of claim 1, wherein S and Y each independently represent a hydrogen atom; Z represents a chlorine atom; and R represents a lower alkyl group having 1 to 4 carbon atoms.

5. The maleimide derivative of claim 1, wherein X is located at the 2-position of the phenyl group and represents a hydrogen atom or a chlorine atom; Y is located at the 4-position of the phenyl group and represents a chlorine atom; Z represents a chlorine atom; and R represents a lower alkyl group having 1 to 4 atoms.

6. The maleimide derivative of claim 1, wherein X represents a fluorine atom; Y represents a hydrogen atom; Z represents a chlorine atom; and R represents a lower alkyl group having 1 to 4 carbon atoms.

7. The maleimide derivative of claim 1, wherein X represents a trifluoromethyl group; Y represents a hydrogen atom; Z represents a chlorine atom; and R represents a lower alkyl group having 1 to 4 carbon atoms.

8. A method for destroying or inhibiting the growth of fungi comprising contacting an effective amount of a maleimide derivative having the formula (I):

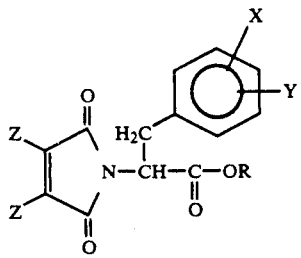
(I)

with a disease producing microorganism, wherein

X and Y each independently represent a hydrogen atom, a halogen atom, a hydroxyl group, a lower alkyl group having 1 to 3 carbon atoms, a lower alkoxy group having 1 to 3 carbon atoms, an aralkyloxy group having 7 to 10 carbon atoms, or a trifluoromethyl group, Z represents a chlorine atom or bromine atom, and R represents a straight or branched alkyl group having 1 to 15 carbon atoms, an alkenyl group having 2 to 5 carbon atoms, an alkynyl group having 2 to 5 carbon atoms, an alkoxyalkyl group having 2 to 5 carbon atoms, an oxoalkyl group having 3 to 6 carbon atoms or a phenyl group which may be substituted with halogen atom, $C_1$-$C_3$ alkyl group or $C_1$-$C_3$ haloalkyl group or a phenyl $C_1$-$C_3$ alkyl group which may be substituted with halogen atom, $C_1$-$C_3$ alkyl group of $C_1$-$C_3$ haloalkyl group.

9. The method of claim 8, further comprising mixing said maleimide derivative in a carrier therefor.

10. The method of claim 8, wherein X represents a hydrogen atom, a chlorine atom, a fluorine atom or a trifluoromethyl group; Y represents a hydrogen atom or a chlorine atom; Z represents a chlorine atom or bromine atom; and R represents a lower alkyl group having 1 to 4 carbon atoms.

11. The method of claim 8, wherein X and Y each independently represent a hydrogen atom; Z represents a chlorine atom; and R represents a lower alkyl group having 1 to 4 carbon atoms.

12. The method of claim 8, wherein X is located at the 2-position of the phenyl group and represents a hydrogen atom or a chlorine atom; Y is located at the 4-position of the phenyl group and represents a chlorine atom; Z represents a chlorine atom; and R represents a lower alkyl group having 1 to 4 carbon atoms.

13. The method of claim 8, wherein X represents a fluorine atom; Y represents a hydrogen atom; Z represents a chlorine atom; and R represents a lower alkyl group having 1 to 4 carbon atoms.

14. The method of claim 8, wherein X represents a trifluoromethyl group; Y represents a hydrogen atom; Z represents a chlorine atom; and R represents a lower alkyl group having 1 to 4 carbon atoms.

* * * * *